United States Patent [19]
Levene et al.

[11] Patent Number: 6,103,255
[45] Date of Patent: Aug. 15, 2000

[54] POROUS POLYMER SCAFFOLDS FOR TISSUE ENGINEERING

[75] Inventors: Howard B. Levene, Piscataway; Christelle M. Lhommeau; Joachim B Kohn, both of Highland Park, all of N.J.

[73] Assignee: Rutgers, The State University, New Brunswick, N.J.

[21] Appl. No.: 09/293,118

[22] Filed: Apr. 16, 1999

[51] Int. Cl.[7] .............................. A61F 2/00; C12N 11/00; C08J 9/26; C08J 9/28

[52] U.S. Cl. .......................... 424/426; 435/174; 435/180; 435/182; 521/61; 521/64; 623/16

[58] Field of Search ................................ 521/61, 64, 916; 435/174, 180, 182; 424/426; 623/16

[56] References Cited

U.S. PATENT DOCUMENTS

| | | | |
|---|---|---|---|
| 2,772,322 | 11/1956 | Witt et al. | 521/61 |
| 2,846,727 | 8/1958 | Bechtold | 521/61 |
| 3,536,796 | 10/1970 | Rock | 521/61 |
| 4,826,945 | 5/1989 | Cohn et al. | 528/76 |
| 5,099,060 | 3/1992 | Kohn et al. | 560/40 |
| 5,149,579 | 9/1992 | Park et al. | 521/79 |
| 5,180,751 | 1/1993 | Park et al. | 521/79 |
| 5,198,507 | 3/1993 | Kohn et al. | 525/432 |
| 5,216,115 | 6/1993 | Kohn et al. | 528/176 |
| 5,332,761 | 7/1994 | Paquet et al. | 521/79 |
| 5,369,137 | 11/1994 | Paquet et al. | 521/79 |
| 5,514,378 | 5/1996 | Mikos et al. | 424/425 |
| 5,587,507 | 12/1996 | Kohn et al. | 560/40 |
| 5,658,995 | 8/1997 | Kohn et al. | 525/432 |
| 5,670,602 | 9/1997 | Kohn et al. | 528/176 |
| 5,686,091 | 11/1997 | Leong et al. | 424/426 |
| 5,723,508 | 3/1998 | Healy et al. | 521/61 |

FOREIGN PATENT DOCUMENTS

WO 94/25079  11/1994  WIPO.

OTHER PUBLICATIONS

Reed et al., "Biodegradable Elastomeric Biomaterials–Polyethylene Oxide/Polyethylene Terephthalate Copolymers," *Trans. Am. Soc. Artif. Intern. Organs*, 23 109–114 (1977).

deGroot et al., "Use of porous biodegradable polymer implants in meniscus reconstruction. 1) Preparation of porous biodegradable polyurethanes for the reconstruction of meniscus lesions," *Colloid Polym. Sci.*, 268, 1073–1081 (1990).

Mikos et al., "Preparation and characterization of poly(L-–lactic acid) foams," *Polymer*, 35, 1068–77 (1994).

Laurenein et al., "A highly porous 3–dimensional polyphosphazene polymer matrix for skeletal tissue regeneration," *Journal of Biomedical Materials Research*, 30, 133–138 (1996).

Schugens et al., "Polylactide macroporous biodegradable implants for cell transplantation. II. Preparation of polylactide foams by liquid–liquid phase separation," *Journal of Biomedical Materials Research*, 30, 449–461 (1996).

*Primary Examiner*—Morton Foelak
*Attorney, Agent, or Firm*—Synnestvedt & Lechner LLP

[57] ABSTRACT

Biodegradable and biocompatible porous scaffolds characterized by a substantially continuous polymer phase, having a highly interconnected bimodal distribution of open pore sizes with rounded large pores of about 50 to about 500 microns in diameter and rounded small pores less than 20 microns in diameter, wherein the small pores are aligned in an orderly linear fashion within the walls of the large pores. Methods of preparing polymeric tissue scaffolds are also disclosed.

12 Claims, 1 Drawing Sheet

POROUS POLYMER SCAFFOLDS FOR TISSUE ENGINEERING

TECHNICAL FIELD

The present invention relates to biodegradable porous polymer scaffolds useful for tissue engineering and tissue guided regeneration. In particular, the present invention relates to biodegradable porous polymer scaffolds with a bimodal distribution of open pore sizes providing a high degree of interconnectivity, high internal surface area, and linearly aligned pores along the walls of the larger pores. The present invention further relates to methods for preparing the scaffolds to obtain the orderly bimodal pore distribution.

BACKGROUND ART

Synthetic degradable polymer scaffolds have been proposed as a new means of tissue reconstruction and repair. The scaffold serves as both physical support and adhesive substrate for isolated cells during in vitro culturing and subsequent in vivo implantation. Scaffolds are utilized to deliver cells to desired sites in the body, to define a potential space for engineered tissue, and to guide the process of tissue development. Cell transplantation on scaffolds has been explored for the regeneration of skin, nerve, liver, pancreas, cartilage and bone tissue using various biological and synthetic materials.

In an alternate approach, degradable polymeric scaffolds are implanted directly into a patient without prior culturing of cells in vitro. In this case, the initially cell-free scaffold needs to be designed in such a way that cells from the surrounding living tissue can attach to the scaffold and migrate into it, forming functional tissue within the interior of the scaffold.

A variety of synthetic biodegradable polymers can be utilized to fabricate tissue engineering scaffolds. Poly (glycolic acid) (PGA), poly(lactic acid) (PLA) and their copolymers are the most commonly used synthetic polymers in tissue engineering. However, in principle, any biodegradable polymer that produces non-toxic degradation products can be used. The potential utility of a polymer as a tissue engineering substrate is primarily dependent upon whether it can be readily fabricated into a three-dimensional scaffold. Therefore, the development of processing techniques to prepare porous scaffolds with highly interconnected pore networks has become an important area of research.

Solvent casting is one of the most widely used processes for fabricating scaffolds of degradable polymers (see Mikos et al., *Polymer*, 35, 1068–77, (1994); de Groot et al., *Colloid Polym. Sci.*, 268, 1073–81 (1991); Laurencin et al., *J Biomed. Mater. Res.*, 30, 133–8 (1996)). U.S. Pat. No. 5,514,378 discloses the basic procedure in which a polymer solution is poured over a bed of salt crystals. The salt crystals are subsequently dissolved away by water in a leaching process. De Groot et al. disclose a modified leaching technique in which the addition of a co-solvent induces a phase separation of the system upon cooling through liquid-liquid demixing. While this separation mechanism leads to the formation of round pores embedded within the polymer matrix, most of the pores are of insufficient size to form a highly interconnected network between the larger pores formed by leaching.

The existing processing methods produce poor scaffolds with a low interconnectivity, especially when a basic leaching method, such as the method disclosed in U.S. Pat. No. 5,514,378, is used. Particles, when dispersed in a polymer solution, are totally covered by the solution, limiting the interconnectivity of the pores within the scaffolds.

U.S. Pat. No. 5,686,091 discloses a method in which biodegradable porous polymer scaffolds are prepared by molding a solvent solution of the polymer under conditions permitting spinodal decomposition, followed by quenching of the polymer solution in the mold and sublimation of the solvent from the solution. A uniform pore distribution is disclosed. A biomodal pore distribution would increase the degree of pore interconnectivity by creating additional channels between the pores, thereby increasing total porosity and surface area.

U.S. Pat. No. 5,723,508 discloses a method in which biodegradable porous polymer scaffolds are prepared by forming an emulsion of the polymer, a first solvent in which the polymer is soluble, and a second polymer that is immiscible with the first solvent, and then freeze-drying the emulsion under conditions that do not break the emulsion or throw the polymer out of solution. This process, however, also produces a more uniform pore size distribution, with the majority of the pores ranging from 9 to 35 microns in diameter.

There remains a need for biodegradable porous polymer scaffolds for tissue engineering having a bimodal pore size distribution providing a highly interconnected pore network, as well as methods by which such scaffolds may be made. Based on a more advanced scientific rationale, polymeric scaffolds with a bimodal pore size distribution may have significant advantages. Pores in the size range of 50 to 500 micron diameter provide sufficiently open space for the formation of functional tissue within the scaffold while the presence of a large number of smaller pores forming channels between the larger pores would increase cell-cell contact, diffusion of nutrients and oxygen to the cells, removal of metabolic waste away from the cells, and surface patterning to guide the cells. This new design concept for degradable polymeric scaffolds requires the presence of a bimodal pore size distribution with larger pores of 50 to 500 micron diameter and smaller pores creating channels between the larger pores.

SUMMARY OF THE INVENTION

This need is met by the present invention. A process is provided that allows fabrication of polymer scaffolds with novel architectures for tissue engineering through a combination of phase separation and leaching techniques.

According to one aspect of the present invention, a biodegradable and biocompatible porous scaffold is provided having a substantially continuous polymer phase with a highly interconnected bimodal distribution of rounded large and small open pore sizes, in which the large pores have a diameter between about 50 and about 500 microns, and the small pores have a diameter less than 20 microns, wherein the small pores are aligned in an orderly linear fashion within the walls of the large pores. The pore interconnectivity is greatly enhanced by the presence of the small pores, which form channels between the large pores. This results in a porosity greater than about 90% and a high specific pore surface area in excess of 10 $m^2/g$.

The network of small pores is created in the walls of the large pores, and is unexpectedly well oriented in a linear array. This provides surface patterning for guiding cell growth throughout the scaffold. This specific architecture also provides a large surface area and internal volume that is ideal for cell seeding, cell growth and the production of extra-cellular matrices. Furthermore, the high interconnectivity of the pores allows for distribution of pores throughout the scaffold, transmission of cell-cell signaling molecules across the scaffolds, diffusion of nutrients throughout the structure, and the patterning of the surface to guide cell growth. Pore diameter and interconnecting structure are essential to vascularization and tissue ingrowth.

The open porosity of the three-dimensional structure maximizes diffusion and permits vascular ingrowth into the implanted scaffold. Ideally, the polymer is completely resorbed over time, leaving only the newly-formed tissue.

The polymer scaffolds of the present invention are prepared from homogenous solutions of biodegradable polymers in a mixture of a first solvent in which the polymer is soluble, and a second solvent in which the polymer is insoluble, but which is miscible with the first solvent. The homogenous solutions are cast on water-soluble particles that are between about 50 and about 500 microns in diameter, and then phase separated by quenching at a low temperature and freeze-drying, followed by leaching. The bimodal distribution of pore diameters results from the larger pores being created by leaching and the smaller pores being created by crystallization upon phase separation of the solvent in which the polymer is soluble.

Therefore, according to another aspect of the present invention, a method is provided for the preparation of biodegradable and biocompatible porous polymer scaffolds in which a biocompatible polymer is dissolved in a miscible solvent mixture of a first solvent in which the polymer is soluble and a second solvent in which the polymer is insoluble, wherein the ratio of first solvent to second solvent is in a range within which the polymer dissolves to form a homogenous solution, and the first solvent has a melting point between about −40 and about 20° C. The homogenous solution is then placed into a form containing water-soluble non-toxic particles that are insoluble in organic solvents and have a diameter between about 50 and about 500 microns. The solution is then quenched at a rate effective to result in crystallization of the first solvent before the onset of liquid-liquid demixing of the polymer solution. The solvents are then sublimated from the polymer phase, after which the particles are removed by leaching with a solvent in which the particles are soluble and the polymer is insoluble.

It is believed that the linear micro-structure results from crystallization of the first solvent in the presence of the second solvent at the surface of the particles. This results in highly porous scaffold foams having a large surface area and large internal volume.

The foregoing and other objects, features and advantages of the present invention are more readily apparent from the detailed description of the preferred embodiments set forth below, taken in conjunction with the accompanying drawing.

BEST MODE OF CARRYING OUT THE INVENTION

Figure 1:
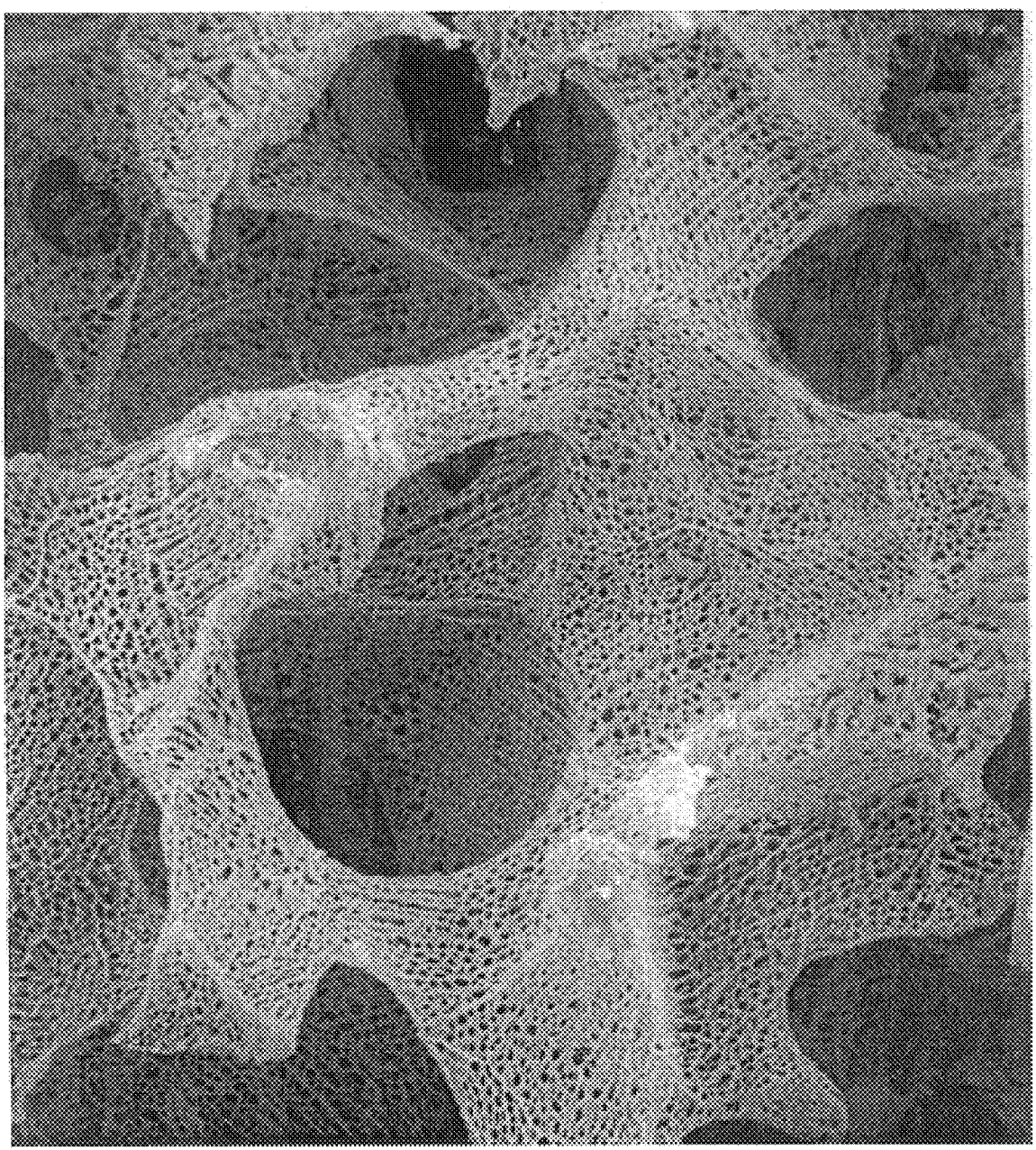
FIG. 1 is a SEM micrograph of a foam prepared by the method of the present invention.

The invention employs thermally induced phase separation to fabricate highly porous biodegradable scaffolds with optimized properties for tissue engineering. Depending upon the thermodynamics, the kinetics and the rate of cooling, phase separation will occur either by solvent crystallization or liquid-liquid demixing. This invention employs solvents and processing conditions under which solvent crystallization predominates as the phase separation mechanism to obtain a porous polymer scaffold with a bimodal pore diameter distribution providing a high degree of pore interconnectivity and a highly linearly ordered architecture of small pores within the walls of the larger pores.

For solvent crystallization to occur before liquid-liquid demixing the selection of solvents and processing conditions are critical. A mixture of two solvents is employed, one in which the polymer is soluble (referred to here for purposes of clarity as "first solvent"), and one in which the polymer is insoluble (referred to here for purposes of clarity as the "second solvent"). The first and second solvents must be miscible, and must form mixtures in which the polymer is soluble, despite its insolubility in the second solvent. Quantities of polymer, first solvent and second solvent are selected to provide a uniform, homogenous solution.

The first solvent should have a melting point between about −40 and about 20° C. Within this range, at a high rate of cooling, crystallization is the favored phase separation mechanism. A melting point between about −20 and about +20° C. is preferred. A solvent that ideally fits these requirements is 1,4-dioxane. It has a melting point of 12° C. and a low crystallization energy.

While not being bound by any particular theory, it is believed that the crystallization is initiated by the second solvent, which is believed to be acting as a nucleating agent. Solvents in which the polymer is insoluble that are suitable for use as the second solvent include water and alcohols such as, but not limited to, methanol, ethanol, isopropanol, tert-butanol and 1,3-propanediol. It is critical that the polymer be soluble in the solvent mixture.

The most preferred pair of first and second solvents consists of 1,4-dioxane and water. When the cooling rate is high, it is believed that the crystallization of 1,4-dioxane is favored. In addition, it is believed that the 1,4-dioxane crystallization is initiated by water, which is believed to be acting as a nucleating agent for the crystallization.

Polymers used for tissue engineering scaffolds must be biocompatible and biodegradable in addition to acting as adhesive substrates for cells, promoting cell growth and allowing retention of differentiated cell function. Such materials must also possess physical characteristics allowing for large surface to volume ratios, mechanical strength and easy processing into complex shapes, such as for bone substitutes. The resulting polymeric device should also be rigid enough to maintain the desired shape under in vivo conditions.

Polymers that are suitable for use in the present invention are substantially biodegradable, non-toxic and physiologically compatible. The polymer must be selected for biocompatibility at the time of implant, and the products of its degradation process must also be biocompatible. Additional parameters that play an important role include the mechanical properties of the material, especially its mechanical rigidity. Relatively high rigidity is advantageous so that the scaffold can withstand the contractile forces exerted by cells growing within the scaffold. Also important are the thermal properties, especially the glass transition temperature, $T_g$, which must be high enough so that the network of pores in the scaffold does not collapse upon solvent removal. It is also important that the biodegradation kinetics of the polymer match the rate of the healing process.

Examples of suitable polymers include α-hydroxycarboxylic acids and copolymers thereof, including PGA, PLA and copolymers thereof; the polyethylene oxide/polyethylene terephthalate disclosed by Reed et al., *Trans. Am. Soc. Artif. Intern. Organs,* page 109 (1977); and the copolymers of lactic or glycolic acid or combinations of the two with hydroxy-ended flexible chains, preferably poly(alkylene glycols) of various molecular weights, disclosed by U.S. Pat. No. 4,826,945. Other suitable polymers include biodegradable and biocompatible polycaprolactones, polyhydroxybutyrates and copolymers of polyesters, polycarbonates, polyanhydrides and poly (ortho esters).

Bisphenol-A based polyphosphoesters have also been suggested for use in biodegradable scaffold design. Such polymers include poly(bisphenol-A phenylphosphate), poly(bisphenol-A ethylphosphate), poly(bisphenol-A ethylphosphonate), poly(bisphenol-A phenylphosphonate), poly[bis(2-ethoxy)hydrophosphonic terephthalate], and copolymers of bisphenol-A based poly(phosphoesters). Although these polymers have been suggested in U.S. Pat. No. 5,686,091, the known cytotoxicity of bisphenol-A make them less preferred candidates for implantation. On the other hand, another useful polymer system is the copolymers of polyethylene oxide/polyethylene terephthalate.

Particularly preferred polymers for the practice of the invention are polymers of tyrosine-derived diphenol compounds. Methods for preparing the tyrosine-derived diphenol monomers are disclosed in U.S. Pat. Nos. 5,587,507 and 5,670,602, the disclosures of both of which are incorporated herein by reference. The preferred diphenol monomers are des-aminotyrosyl-tyrosine (DT) esters. These monomers have a free carboxylic acid group that can be used to attach a pendent chain. Usually, various alkyl ester pendent chains are employed. For purposes of the present invention, the ethyl ester is referred to as DTE, the butyl ester as DTB, the hexyl ester as DTH, the octyl ester as DTO, the benzyl ester as DTBn, and so forth.

The tyrosine-derived diphenol compounds are used as monomeric starting materials for polycarbonates, polyiminocarbonates, polyarylates, polyurethanes, polyethers, and the like. Polycarbonates, polyiminocarbonates and methods of preparation are disclosed by U.S. Pat. Nos. 5,099,060 and 5,198,507, the disclosures of which are incorporated herein by reference. Polyarylates and methods of preparation are disclosed by U.S. Pat. No. 5,216,115, the disclosure of which is also incorporated herein by reference. Block copolymers of polycarbonates and polyarylates with poly(alkylene oxides) and methods of preparation are disclosed by U.S. Pat. No. 5,658,995, the disclosure of which is also hereby incorporated by reference. Strictly alternating poly(alkylene oxide ether) copolymers and methods of preparation are disclosed by International Application No. PCT/US98/23737 filed Nov. 6, 1998, the disclosure of which is also incorporated herein by reference.

Other particularly preferred polymers include the polycarbonates, polyimino-carbonates, polyarylates, polyurethanes, strictly alternating poly(alkylene oxide ethers) and poly(alkylene oxide) block copolymers polymerized from dihydroxy monomers prepared from α-, β- and γ-hydroxy acids and derivatives of tyrosine. The preparation of the dihydroxy monomers and methods of polymerization are disclosed by International Patent Application No. PCT/US98/036013, the disclosure of which is also incorporated herein by reference.

Polycarbonates, polyimino carbonates, polyarylates, poly(alkylene oxide) block copolymers and polyethers of the diphenol and dihydroxy tyrosine monomers that contain iodine atoms or that contain free carboxylic acid pendent chains may also be employed. Iodine-containing polymers are radio-opaque. These polymers and methods of preparation are disclosed by International Patent Application No. PCT/US98/23777 filed Nov. 6, 1998. Polymers containing free carboxylic acid pendent chains and methods of preparation are disclosed by U.S. patent application Ser. No. 09/56,050, filed Apr. 7, 1998. The disclosures of both applications are also incorporated herein by reference.

In the method for making the biodegradable scaffolds for tissue engineering, the polymer is first dissolved in the mixture of miscible solvents. The amount of the second solvent should be that quantity effective to induce phase separation on cooling, but less than the amount effective to induce phase separation before starting the procedure. The volume ratio of the first solvent to the total volume of solvent, is preferably between about 1 to about 40% v/v, and more preferably between about 5 to about 15% v/v.

The polymer concentration in the solvent mixture is preferably between about 0.5 and about 25 weight %, and more preferably between about 10 and about 20 weight %. The concentration of polymer in the solvent should be selected to ensure adequate diffusion of the polymer solution through the particles for the formation of the large pores.

The particles are essentially any non-toxic biocompatible crystalline substance that is readily water-soluble and insoluble in organic solvents. Examples of suitable particles include biologically acceptable alkali metal and alkaline earth metal halides, phosphates, sulfates, and the like. Crystals of sugars may also be used, as well as microspheres of water-soluble polymers, or proteins, such as albumin. Sodium chloride is a particularly preferred particle. Particles should be selected having the diameter that is desired for the large pores of the bimodal distribution of pore sizes. Particles having a particle size diameter between about 50 and about 500 microns are preferred, and diameters between about 200 and about 400 microns are more preferred.

The solution of polymer and solvent is poured on particles sieved to the desired diameter between about 50 and about 500 microns. The particles are in an appropriate mold, such as a dish.

After the diffusion of the polymer solution through the particles, the contents of the dish is rapidly cooled at a rate effective to induce crystallization of the first solvent before the onset of liquid-liquid demixing of the polymer solution. For example, the dish can be dropped in liquid nitrogen or an equivalent cryogenic liquid and maintained in the liquid nitrogen for a rapid and complete quenching of the system.

The dish is then placed in a vessel connected to a vacuum pump for the time needed for complete sublimation of the solvents. This step allows the removal of the solvent by sublimation from the frozen materials so that it leaves a porous structure. The system is still frozen and the polymer does not relax during solvent removal.

Finally, the particles are leached with a solvent in which they are soluble, and in which the polymer is soluble, for example, the second solvent, or, more preferably, water, regardless of whether or not it is employed as the second solvent. The leaching solvent is changed several times to ensure complete removal of the particles. The resulting scaffolds are removed from the leaching solvent and dried to constant weight.

The method provides a bimodal distribution of large and small pore sizes. The large pores are the impressions of the particles on the which the polymer solution is cast. As noted above, the large pores have an average pore diameter between about 50 and about 500 microns. The small pores are formed when the polymer solution undergoes phase separation under cooling and have an average diameter less than about 20 microns. Preferred methods according to the present invention provide the small pores having an average diameter less than about 10 microns. The shape of the larger pores can be smoothed by the addition of water to the polymer solution if water is the non-solvent.

The porosity of the resulting scaffolds is greater than about 90%. Preferred methods of the present invention provide scaffold foams having a porosity greater than about 95%. The scaffolds have a specific pore surface area in excess of 10 m$^2$/g, and preferred methods result in the formation of specific pore surface areas in excess of 20 m$^2$/g.

Scaffolds can also be further modified after fabrication. For example, the scaffolds can be coated with bioactive substances that function as receptors or chemoattractors for a desired population of cells. The coating can be applied through absorption or chemical bonding.

Particularly preferred scaffolds incorporate additives for subsequent release in a controlled fashion. The additive may be released by a bioerosion of the polymer phase, or by diffusion from the polymer phase. Alternatively, the additive may migrate to the polymer surface of the scaffold structure, where it is active.

The polymer and the first and second solvents may be pre-blended before the additive is dissolved therein. Alternatively, the additive may be dissolved in the solvent in which it is most soluble, after which the first and second solvents and polymer are combined.

The additive may be provided in a physiologically acceptable carrier, excipient, stabilizer, etc., and may be provided in sustained release or timed release formulations. The additives may also incorporate agents to facilitate their delivery, such as antibodies, antibody fragments, growth factors, hormones, or other targeting moieties, to which the additives are coupled.

Acceptable pharmaceutical carriers for therapeutic use are well known in the pharmaceutical field, and are described, for example, in *Remington's Pharmaceutical Science*, Mac Publishing Co., (A. R. Gennaro edt. 1985). Such materials are non-toxic to recipients at the dosages and concentrations employed, and include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin or immunoglobulins, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium and/or non-ionic surfactants such as tween, pluronics or PEG.

The additive may be covalently attached to polymers having pendent free carboxylic acid groups. Detailed chemical procedures for the attachment of various moieties to polymer bound free carboxylic acid groups have been described in the literature. See, for example, U.S. Pat. Nos. 5,219,564 and 5,660,822; Nathan et al., *Bio. Cong. Chem.*, 4, 54–62 (1992) and Nathan, *Macromolecules*, 25, 4476 (1992). The disclosures of both patents and both journal articles are incorporated herein by reference. These publications disclose procedures by which polymers having pendent free carboxylic acid groups are reacted with moieties having reactive functional groups, or that are derivatized to contain active functional groups, to form a polymer conjugate.

Hydrolytically stable conjugates are utilized when the additive is active in conjugated form. Hydrolyzable conjugates are utilized when the additive is inactive in conjugated form.

An amount of additive is incorporated into the porous polymer scaffold that will provide optimal efficacy to the subject in need of treatment, typically a mammal. The dose and method of administration will vary from subject to subject and be dependent upon such factors as the type of mammal being treated, its sex, weight, diet, concurrent medication, overall clinical condition, the particular compounds employed, the specific use for which these compounds are employed and other factors which those skilled in the art will recognize. The porous polymer scaffolds can be utilized in vivo as tissue engineering and tissue guided regeneration scaffold in mammals such as primates, including humans, sheep, horses, cattle, pigs, dogs, cats, rats and mice, or in vitro. The polymer-drug combinations of this invention may be prepared for storage under conditions suitable for the preservation of drug activity as well as maintaining the integrity of the polymers, and are typically suitable for storage at ambient or refrigerated temperatures. The porous polymer scaffolds to be used for tissue engineering and tissue guided regeneration must also be sterile. Sterility may be readily accomplished by conventional methods such as irradiation or treatment with gases or heat.

Additives suitable for use with the present invention include biologically or pharmaceutically active compounds. Examples of biologically active compounds include cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-β and the like.

Examples of pharmaceutically active compounds include, for example, acyclovir, cephradine, malfalen, procaine, ephedrine, adriomycin, daunomycin, plumbagin, atropine, quanine, digoxin, quinidine, biologically active peptides, chlorin e$_6$, cephalothin, proline and proline analogues such as cis-hydroxy-L-proline, penicillin V, aspirin, ibuprofen, steroids, nicotinic acid, chemodeoxycholic acid, chlorambucil, and the like. Therapeutically effective dosages may be determined by either in vitro or in vivo methods. For each particular additive, individual determinations may be made to determine the optimal dosage required. The determination of effective dosage levels, that is, the dosage levels necessary to achieve the desired result, will be within the ambit of one skilled in the art. The release rate of the additives may also be varied within the routine skill in the art to determine an advantageous profile, depending on the therapeutic conditions to be treated.

A typical additive dosage might range from about 0.001 mg/kg to about 1000 mg/kg, preferably from about 0.01 mg/kg to about 100 mg/kg, and more preferably from about 0.10 mg/kg to about 20 mg/kg. The additives may be used alone or in combination with other therapeutic or diagnostic agents.

The porous polymer scaffolds of the present invention are characterized by scanning electron microscopy (SEM) and mercury porosimetry. Specific examples are provided below.

The porous polymer scaffolds are shaped into articles for tissue engineering and tissue guided regeneration applications, including reconstructive surgery. The structure of the scaffold allows generous cellular ingrowth, eliminating the need for cellular preseeding. The porous polymer scaffolds may also be molded to form external scaffolding for the support of in vitro culturing of cells for the creation of external support organs.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support. The scaffold polymer is selected to degrade as the need for an artificial support diminishes.

In the reconstruction of structural tissues like cartilage and bone, tissue shape is integral to function, requiring the molding of the porous polymer scaffold into articles of varying thickness and shape. Any crevices, apertures or refinements desired in the three-dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumenary, arteriovenous, urinary or any other tissue forming solid or hollow organs.

The scaffold may also be used in transplantation as a matrix for dissociated cells such as chondrocytes or hepatocytes to create a three-dimensional tissue or organ. Any type of cell can be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue can also be used, which may provide a number of different cell types in the same structure.

The cells are obtained from a suitable donor, or the patient into which they are to be implanted, dissociated using standard techniques and seeded onto and into the foam scaffold. In vitro culturing optionally may be performed prior to implantation. Alternatively, the foam scaffold is implanted, allowed to vascularize, then cells are injected into the scaffold. Methods and reagents for culturing cells in vitro and implantation of a tissue scaffold are known to those skilled in the art.

INDUSTRIAL APPLICABILITY

The porous polymer scaffolds of the present invention may be fabricated into useful articles for tissue engineering and tissue guided regeneration applications, including reconstructive surgery. The scaffolds may also be molded to form external scaffolding for the support of in vitro culturing of cells for the creation of external support organs. The scaffolds may also be used in transplantation as a matrix for dissociated cells.

The following non-limiting examples set forth hereinbelow illustrate certain aspects of the invention. All parts and percentages are by weight unless otherwise noted and all temperatures are in degrees Celsius.

EXAMPLES

Examples 1–6

Preparation of Scaffolds from different Polymers

Porous scaffolds were prepared from the polymers listed in Table 1:

TABLE 1

|  | Mw (daltons) | Polymer concentration g/l |
|---|---|---|
| Poly(DTE carbonate) | 206,000 | 60.6 |
| Poly(DTE carbonate) | 89,000 | 92.7 |
| Poly(DTE co 30% DT carbonate) | 96,000 | 87.6 |
| Poly(DTE co 5% PEG 1K carbonate) | 88,000 | 74.5 |
| Poly(DTB succinate) | 108,000 | 90.7 |
| Poly(L-lactic acid) | 93,000 | 91.5 |

Example 1

Preparation of Poly(DTE c) Scaffolds

Materials:

Poly(DTE carbonate) (Mw=206,000) was prepared using the method disclosed by U.S. Pat. No. 5,099,060. 1,4-dioxane (certified ACS grade) and sodium chloride (NaCl) crystal were purchased from Fisher Scientific (Pittsburgh, Pa.). The crystals were sieved with USA standard testing sieves (ASTM-E 11, Tyler, Mentor, Ohio) with opening of 212 $\mu$m (ni70) and 425 $\mu$m (ni40). The mercury used in the porosimetry study was triple distilled (Bethlehem Apparatus, Hellertown, Pa.).

Scaffold fabrication:

The scaffold was prepared by the following processing method:

0.2 g of Poly(DTE carbonate) was dissolved in the mixture of 3 ml 1,4-dioxane and 0.3 ml water under magnetic stirring at room temperature. After dissolution of the polymer, the clear solution was poured on 7 grams of sieved sodium chloride salts (average size:~200 $\mu$m—~400 $\mu$m) in an appropriate dish.

After the diffusion of the polymer solution through the salt bed the dish was submerged in liquid nitrogen and maintained for a complete freezing of the system. The dish was then placed in a vessel connected to a vacuum pump for the time needed for complete sublimation of the solvent, leaving a porous structure. The polymer did not relax during solvent removal.

Finally, the salt was leached out in water. The water was changed several times until the sensitive silver nitrate test did not show any additional release of chloride ions into the water. The resulting scaffolds were removed from the water and dried for several days to constant weight.

SEM Scanning Electron Microscopy:

SEM was performed to assess the morphology of the scaffolds. Samples were prepared for SEM by cryofracture of the scaffolds in liquid nitrogen (-196iC). The cryofracture was done on wet samples. The scaffolds were submitted to a series of pressurization-depressurization to ensure the filling of the pores with water. When no more bubbles were coming out of the scaffolds and the samples sank to the bottom of the vial, they were submerged in liquid nitrogen.

Then samples were thoroughly dried under vacuum, mounted on metal stubs using adhesive tabs. They were coated with silver using a Balzers SCD004 sputter coater (BAL-TEC). The gas pressure was set at 3–5.10$^{-2}$ mbar and the current was 30 mA for a coating time of 120 s. An Hitachi S450 SEM at 15 kV was used for examination.

Image analysis:

The size of the pores of the digital images obtained with the SEM was analyzed with the use of NIH Image 1.6 software. Pore area, perimeter, major and minor axis of the ellipse were the image parameters evaluated. Adjustment of the digital images was necessary prior to pore assessment. To ensure equivalent adjustment for all the images, a Pascal macro was written in accordance with the image scale used for the pore size examined.

The numbered pores were compared with the actual digital image to confirm pore location. Certain pore numbers which were not properly represented were excluded from the statistical data analysis. For each scaffold, 3 different digital images at 2 different magnifications (low magnification (scale bar of 200 µm) and high magnification (scale bar of 10 µm)), were analyzed (n=3).

Mercury Porosimetry:

The dried scaffolds were very soft and could be easily deformed because of the high total porosity and the low polymer modulus. Moreover the largest pores which were expected to have a mean diameter around 300 µm (final imprints of the salt), would have been underestimated by this technique. For these reasons, the scaffolds were analyzed as the salt was still inside the polymer matrix.

The pore volume and the pore size distribution were determined by recording mercury intrusion volume into the scaffolds at different pressures with a model 9540 Mercury Porosimeter (Micromeritics, Norcross, Ga.). The filling pressure was recorded up to 3,000 psia. This pressure corresponds to the energy required to intrude mercury into pores of 0.06 µm or larger. The pore diameter and porosity values refer to equivalent cylindrical pores with a diameter smaller than 310 µm.

These values were determined from the Washburn equation:

$$D = -(1/P)4\gamma\cos f$$

wherein D is the pore diameter in microns; P is the applied pressure (psia); $\gamma$ is the surface tension between mercury and the scaffold surface (dynes/cm); and $\phi$ is the contact angle (degrees).

The values recommended for the surface tension and the contact angles are:

g=485 dynes/cm $\phi$=130°

Results are presented as a curve of the incremental mercury intrusion (ml/g) in function of the calculated mean pore diameter. For each scaffold, samples were run in triplicate (n=3).

Discussion of the Results:

TABLE II

Results from SEM image analysis for a poly(DTE carbonate) scaffold

| | Area ($\mu m^2$) | Perimeter ($\mu m$) | Max axis ($\mu m$) | Min axis ($\mu m$) |
|---|---|---|---|---|
| scale: 10 µm | | | | |
| average | 47 | 30 | 9 | 5 |
| stdev | 14 | 5 | 2 | 0 |
| scale: 200 µm | | | | |
| average | 49,554 | 1077 | 300 | 191 |
| stdev | 7,279 | 54 | 21 | 20 |

The poly(DTE carbonate) scaffold is characterized by a bimodal distribution of open pore sizes resulting from different processes (FIG. 1). The largest pores, with an average pore diameter between 200 µm and 400 µm, are the impressions of the salts on which the solution is cast. The smallest pores with an average size lower than 20 µm are formed when the polymer solution undergoes phase separation under cooling. The smallest pores appear on the walls of the largest pores and in the polymer phase between the largest pores.

The network of pores is highly interconnected. An interesting observation from the mercury porosimetry, is that by their own, the smallest pores are highly connected together. Even if the largest pores arc filled with the NaCl salts for measurements, it appears it is possible to reach most of the smallest pores when higher pressures are applied. Moreover, the interconnectivity between the largest pores is enhanced by the presence of the smallest pores which form channels between the largest pores. The porosity of the resulting scaffolds is greater than 90%. The network of the small pores created in the walls of the largest pores is astonishingly well oriented in a linear array.

Example 2

Preparation of Low Molecular Weight Poly(DTE carbonate) Scaffolds

A scaffold was prepared from a lower molecular weight poly(DTE carbonate), to evaluate its total specific surface area and to estimate its porosity.

Materials:

The poly(DTE carbonate) (Mw=89,0000) was prepared as in Example 1.

Scaffold Fabrication:

0.3 g of the lower molecular weight poly(DTE carbonate) was dissolved in a solution of 1,4-dioxane and water (91/9% v/v). The solution was fabricated into a scaffold as in Example 1.

BET Measurement: Total Specific Surface Area Measurement:

Specific surface area was investigated using the Brunauer-Emmett-Teller (BET) technique utilizing a Quantasorb (Quantachrome, Boynton Beach, Fla.). The BET apparatus determines the total specific surface area of the sample by calculating the amount of nitrogen adsorbed on the surface.

Porosity Estimation:

For scaffolds with large pore sizes (like as those used in this study) Hg porosimeter underestimates the porosity. A more accurate determination of porosity is possible by measuring the weight, height and diameter of each sample. From these measurements, the apparent density of the scaffold (p*) may be calculated and the porosity ($\epsilon$) determined by:

$$\epsilon = 1 - \rho P^* / \rho_{PDTEC}$$

where $\rho_{PDTEC}$ is the polymer density (1.2778).

Results:

The total pore surface area of the poly(DTE carboante) scaffold was nearly 20 $m^2/g$. This value is 10 times higher than the value (obtained by mercury porosimetry) reported for scaffolds prepared by spraying PLLA solutions in naphthalene. This value is in the range of the values (16 to 99 $m^2/g$) (obtained by mercury porosimetry) reported for scaffolds prepared by an emulsion technique from a PLGA solution in methylene chloride but with a mean diameter lower than 50 µm. The estimated porosity was 97%.

Example 3

Preparation of Poly(DTE co 30%DT Carbonate) Scaffolds

In this example, the methodology illustrated in Example 1 is used to prepare scaffolds from a free acid copolymer: poly(DTE co 30%DT carbonate)

Materials:

Poly(DTE co 30% DT carbonate) (Mw=96,0000) was prepared using the method disclosed by U.S. patent application Serial No. 09/056,050 filed Nov. 7, 1997, the disclosure of which is hereby incorporated by reference.

Scaffold Fabrication:

0.289 g of poly(DTE co 30%DT carbonate) was dissolved in 1,4-dioxane/water (91/9% v/v). The solution was fabricated into a scaffold as in Example 1.

SEM, Mercury Porosimetry and Image Analysis:

The poly(DTE co 30%DT carbonate) scaffold was compared with the poly(DTE carbonate) scaffolds from example 1.

Results:

From the SEM image analysis and the mercury porosimetry results, it can be concluded that the scaffolds prepared from poly(DTE carbonate) and poly(DTE co 30% DT carbonate) present similar pore size distribution. No significant difference was observed between the two scaffolds. From the point of view of the techniques used to characterize the scaffolds, by controlling the viscosity of the polymer solution, it is possible to prepare scaffolds with similar pore size distribution from poly(DTE carbonate) and poly(DTE co 30%DT carbonate)

Example 4

Preparation of Poly(DTE co 5%PEG 1000 Carbonate) Scaffolds

In this example, the methodology illustrated in Example 1 is used to prepare scaffolds from a copolymer of PEG and poly(DTE carbonate), poly(DTE co 5% PEG1000 carbonate).

Materials:

Poly(DTE co 5% PEG1000 carbonate) (Mw=88,0000) was prepared using the method disclosed by U.S. Pat. No. 5,658,995.

Scaffold fabrication:

0.246 g of poly(DTE co 5%PEG1000 carbonate) was dissolved in 3.3 ml 1,4-di-oxane/water (91/9% v/v). The solution was fabricated into a scaffold as in Example 1.

SEM, Mercury Porosimetry and Image Analysis:

The poly(DTE co 5%PEG1000 carbonate) scaffold was compared with the poly(DTE carbonate) scaffolds from example 1.

Results:

From the SEM image analysis and the mercury porosimetry results, it can be concluded that the scaffolds prepared from poly(DTE carbonate) and poly(DTE co 5% PEG1000 carbonate) present similar pore size distribution. No significant difference was observed between the two scaffolds. From the point of view of the techniques used to characterize the scaffolds, by controlling the viscosity of the polymer solution, it is possible to prepare scaffolds with similar pore size distribution from poly(DTE carbonate) and poly(DTE co 5%PEG1000 carbonate).

Example 5

Preparation of Poly(DTB Succinate) Scaffolds

In this example, the methodology illustrated in Example 1 is used to prepare scaffolds from a polyarylate instead of a polycarbonate. Poly(DTB succinate) is characterized by a lower Tg (65° C.) as compared with the poly(DTE carbonate) (92° C.) of Example 1.

Materials:

Poly(DTB succinate) (Mw=108,0000) was prepared using the method disclosed by U.S. Pat. No. 5,216,115.

Scaffold Fabrication:

0.3 g of poly(DTB succinate) was dissolved in 3.3 ml of a solution of 1,4-dioxane and water (91/9% v/v). The solution was fabricated into a scaffold as in Example 1.

SEM:

The poly(DTB succinate) scaffold was compared with the poly(DTE carbonate) scaffold from example 1.

Results:

From the SEM observation, the poly(DTB succinate) scaffold presents the same morphological characteristics as the poly(DTE carbonate) scaffold from example 1 (see results and discussion from example1).

Example 6

Preparation of poly(L-lactic acid) (PLLA) scaffolds

In this example, the methodology illustrated in Example 1 is used to prepare scaffolds from a PLLA instead of a polycarbonate.

Scaffold Fabrication:

0.3 g of PLLA (Mw=108,000) (Medisorb polymers, Alkermes, Inc., Cincinnati, Ohio) was dissolved in 1,4-dioxane/water (91/9% v/v). The solution was fabricated into a scaffold as in Example 1.

SEM:

The PLLA scaffold was compared with the poly(DTE carbonate) scaffold from example 1.

Results:

From the SEM observation, the PLLA scaffold presents the same morphological characteristics as the poly(DTE carbonate) scaffold from example 1 (see results and discussion from example1).

Example 7

Scaffold Preparation from Solutions with Increasing Amounts of Water

Studies were conducted using the method of this application to optimize the morphology of the porous scaffolds by addition of increasing amounts of water in the polymer solution.

Scaffold Fabrication:

0.3 g of the poly(DTE carbonate) from example 1 was dissolved in 3.3 ml 1,4-di-oxane/water (85/15% v/v). The solution was fabricated into a scaffold as in Example 1.

SEM:

This scaffold was compared with the scaffold prepared in Example 1

Results:

Water acts like a nucleating agent in the 1,4-dioxane crystallization process. Water increases the nucleation density in the initiation step of the crystallization of the solvent when the polymer solution is quenched in the liquid nitrogen. As the nucleation density increases, the size of the resulting crystals is always smaller. This could explain the finer microstructure observed between the largest pores when the proportion of water is increasing. The proportion in volume of the very small pores (mean diameter lower than 5 µm) increases with the amount of water in the solution.

Water is added to encourage the phase separation of the polymer solution under cooling. With increasing water amounts, the polymer solubility in the solvent is gradually reduced. When the solution is quenched, the L—L demixing of the polymer solution is induced earlier. More nuclei can be formed and can grow in the polymer matrix before the complete freezing of the system. Thus, much more round pores (resulting from the L—L demixing) are present in the final scaffolds.

The presence of water in the solution also contributes to the dissolution of the NaCl salts on which the solution is cast. An evolution in the shape of the largest pores as the water proportion increases is observed. Apparently the NaCl salts have been eroded by the process. For this reason, we observe a significant increase in the interconnectivity between the largest pores as the water content increases in the solution.

Example 8

In vivo Cell Growth into the Scaffolds:

The highly porous scaffolds were evaluated in an in vivo animal model. Thirty-two skeletally mature male New Zealand White rabbits had scaffolds implanted bilaterally in their calvaria (skull).

Scaffolds were prepared as in example #2. After preparation, the scaffolds were dried under vacuum, sealed in sterilization pouches, and then placed in an Anprolene AN72C Automated Ventilated Sterilizer for sterilization by ethylene oxide exposure. After sterilization, the samples were allowed to equilibrate in ambient air for at least 2 weeks to ensure the removal of ethylene oxide.

For each surgery, the rabbits were prepared using full sterile technique. Two implants were implanted for each surgery. Each implant was placed into one of two 8 mm diameter defects.

The implanted scaffolds were 8 mm diameter by 2–3 mm thickness to correspond with rabbit calvaria dimensions. The scaffolds were not preseeded with cells. At 2, 4, 8, and 16 weeks, the scaffolds were harvested and analyzed histologically. At half the time point (eg 2 weeks for the 4 week time point), and prior to euthanization, the rabbits were injected with oxytetracycline which labels bone ingrowth. Samples were dehydrated in water/alcohol solutions of 70%, 80%, 95%, and 100% ethanol, cleared with a histological clearing agent (Hemo-De from Fisher), and then fixed in a polymerizing solution of methyl methacrylate (Fisher) so that the sample was embedded in a solid block of polymethylmethacrylate. The samples were cut horizontally and vertically to give a horizontal and vertical cross section. The sections were mounted, ground, and polished to 1–3 cell layers in thickness. The samples were viewed under ultraviolet light and analyzed for ingrowth. The samples were then stained with Stevenel's blue and Van Geison's Picro-Fuschin. In such staining, bone was red, fibrous tissue was blue, and osteoid was green. For both stains, the sample was photographed for visual observation and image analysis.

The depth of bone ingrowth was measured to reflect the effect of the highly porous scaffold architecture and compared to a previous study. The previous study provided data for scaffolds created without the 1–10 micron pores. The older scaffolds were created from the same polymer, but were created using a different solvent with a leaching technique without a rapid cooling step.

At the 3 to 4 week time point, a measurable difference appeared between the two sponge types. The highly porous scaffolds showed a greater amount of bone ingrowth. Additionally, the ordered alignment of the 1–10 micron pores affected cellular alignment. Cells were observed to align in the pattern created by the pores. The cells also mineralized along the pattern as well.

The highly porous scaffolds were superior to prior scaffolds in that they encouraged cell ingrowth and guided cell proliferation beyond what would expected for prior scaffold types.

Example 9

In vivo Cell Growth into Scaffolds. A Comparative Study.

In a comparative in vivo implantation study, using the rabbit skull defect model of Example 8, two different scaffold architectures were compared for their ability to support the growth of new bone into the scaffold. The two scaffold architectures were uniform in pore size (200–500 microns) versus a bimodal pore distribution as described in this invention. Although the scaffolds were identical in all aspects other than the pore size distribution, the scaffolds with bimodal distributions had greater bone healing.

The foregoing examples and description of the preferred embodiment should be taken as illustrating, rather than as limiting, the present invention as defined by the claims. As would readily be appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A method for the preparation of biodegradable and biocompatible porous bimodal polymer scaffolds characterized by:

dissolving from about 0.5 to about 25 weight % of a biocompatible polymer in a miscible solvent mixture of a first solvent in which said polymer is soluble and a second solvent in which said polymer is insoluble, wherein the ratio of said first solvent to said second solvent is in a range within which said polymer dissolves to form a homogenous solution, and the first solvent has a melting point between about −40 and about 20° C.;

placing said polymer solution into a form containing water-soluble non-toxic particles that are insoluble in organic solvents and have a diameter between about 50 and about 500 microns;

quenching said solution at a rate effective to result in crystallization of said first solvent before the onset of liquid-liquid demixing of said first and second solvent;

sublimating said polymer to remove said first and second solvents;

leaching said polymer with a solvent in which said particles are soluble and said polymer is insoluble to remove said particles from said polymer; and drying said polymer.

2. The method of claim 1, characterized in that the ratio of said first solvent to said total solvent volume is between about 1% and about 40% v/v.

3. The method of claim 1, characterized in that said first solvent is 1,4-dioxane and said second solvent is water.

4. The method of claim 1, characterized in that said polymer is selected from the group consisting of biocompatible and biodegradable polycarbonates, polyarylates, block copolymers of polycarbonates with poly(alkylene oxides), block copolymers of polyarylates with poly(alkylene oxides), α-hydroxycarboxylic acids, poly(caprolactones), poly(hydroxybutyrates), polyanhydrides, poly(ortho esters), polyesters, and bisphenol-A based poly(phosphoesters).

5. The method of claim 1, characterized in that said particles are selected from the group consisting of alkali metal and alkaline earth metal halides, phosphates and sulfates, sugar crystals, water-soluble polymer microspheres and protein microspheres.

6. The method of claim 5, characterized in that said particles are sodium chloride crystals.

7. The method of claim 1, characterized in that said quenching step comprises immersing said solution in liquid nitrogen.

8. The method of claim 1, characterized in that said polymer is leached with water.

9. A polymeric tissue scaffold prepared by the method of claim 1.

10. The method of claim 1, characterized in that said polymer comprises an effective amount of a biologically active substance that either promotes or prevents a particular variety of cellular tissue ingrowth.

11. The method of claim 1, characterized in that said polymer comprises an effective amount of a pharmaceutically active compound.

12. A method of regulating cellular attachment, migration and proliferation on a polymeric substrate, characterized by contacting living cells, tissues or biological fluids containing living cells with the scaffold produced in the method of claim 10.

* * * * *